(12) United States Patent
Pinna et al.

(10) Patent No.: US 6,399,192 B1
(45) Date of Patent: Jun. 4, 2002

(54) ADHESIVE PLASTER WITH MICROCAPSULES CONTAINING ESSENCES, AND METHOD FOR ITS PREPARATION

(75) Inventors: Fausto Pinna, Milan; Marco Pinna, Varese, both of (IT)

(73) Assignee: Biofarm S.R.L., Milan (IT)

( * ) Notice: Subject to any disclaimer, the term of this patent is extended or adjusted under 35 U.S.C. 154(b) by 0 days.

(21) Appl. No.: 09/445,455

(22) PCT Filed: Jan. 26, 1999

(86) PCT No.: PCT/EP98/00416

§ 371 (c)(1),
(2), (4) Date: Dec. 16, 1999

(87) PCT Pub. No.: WO98/57613

PCT Pub. Date: Dec. 23, 1998

(30) Foreign Application Priority Data

Jun. 18, 1997 (IT) .......................................... MI97A1430

(51) Int. Cl.[7] .................................................. B32B 7/12
(52) U.S. Cl. ...................... 428/353; 428/354; 428/40.2; 428/41.7; 428/41.9; 424/65; 523/102; 523/111; 427/282
(58) Field of Search ................................ 428/905, 40.2, 428/41.7, 41.9, 352, 354, 353; 424/65; 523/102, 111, 200; 427/282

(56) References Cited

U.S. PATENT DOCUMENTS

| 4,386,135 A | * | 5/1983 | Campbell et al. ............ 428/447 |
| 4,528,226 A | * | 7/1985 | Sweeny ........................ 428/40 |
| 4,654,256 A |   | 3/1987 | Doree et al. |
| 4,959,208 A |   | 9/1990 | Chakrabarti et al. |
| 6,244,265 B1 | * | 6/2001 | Cronk et al. ........... 128/200.24 |

FOREIGN PATENT DOCUMENTS

| EP | 0 188 883   | 7/1986 |
| EP | 0 195 254   | 9/1986 |
| EP | 0 255 799   | 6/1987 |
| WO | WO 93 13938 A | 7/1993 |
| WO | WO 95 26155 A | 10/1995 |

* cited by examiner

*Primary Examiner*—James J. Seidleck
*Assistant Examiner*—Melanie D. Bagwell
(74) *Attorney, Agent, or Firm*—Oblon, Spivak, McClelland, Maier & Neustadt, P.C.

(57) ABSTRACT

Adhesive plaster that may be applied on human skin and that has a number of microcapsules applied on its surface destined to remain exposed to the air, the said microcapsules enclosing liquid essences that are released by the microcapsules when the latter burst as a result of friction, the said microcapsules being applied on the adhesive plaster by means of silk-screen printing and with the use of water-soluble resins.

12 Claims, 1 Drawing Sheet

ADHESIVE PLASTER WITH MICROCAPSULES CONTAINING ESSENCES, AND METHOD FOR ITS PREPARATION

FIELD OF THE INVENTION

The subject of the present invention is an adhesive plaster that may be applied on the skin and that has its surface destined to remain exposed to the air treated in such a way as to release essences having an aromatic, balsamic, deodorant, or similar effect, by the mere rubbing of the said surface.

BACKGROUND OF THE INVENTION

For many years now the technique of micro-encapsulation, which enables the enclosing and conservation of very small quantities of liquid inside micro-capsules, has been well known and widely used, the enclosed liquids being released when the micro-capsules are caused to burst or to dissolve, according to the nature of the material that makes up the external wall of the micro-capsules themselves.

SUMMARY OF THE INVENTION

The main aim of the present invention is to make adhesive plasters on the surface of which (the surface that is destined to remain exposed to the air) are applied micro-capsules containing essences that are released when the micro-capsules themselves burst merely as a result of rubbing, the said essences thus emanating in the air their aroma, which may also have a balsamic, or deodorant, or other effect.

DETAILED DESCRIPTION OF THE INVENTION

Figure 1:
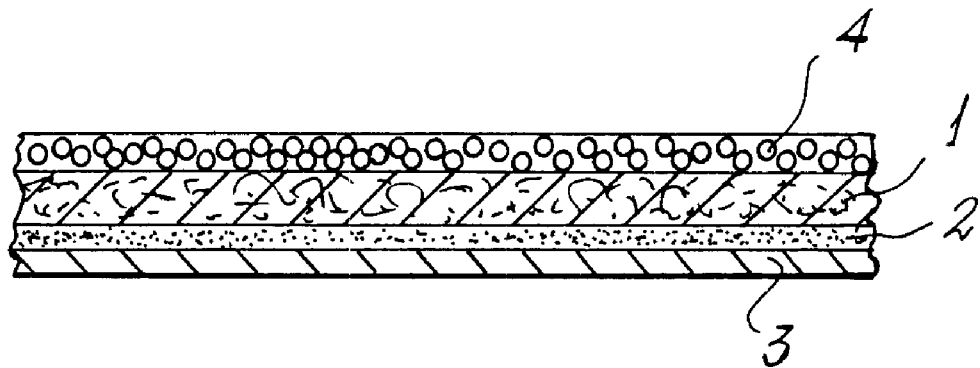
FIGS. 1 and 2 represent a cross section of two different plasters, shown in enlarged scale and out of proportion.

Such an adhesive plaster may be kept exposed to the air for a long time without losing its own characteristics described above. The plaster may be of any traditional shape; for example, it may be made up of a thin strip of fabric which can be applied underneath the armpits, in which case the micro-capsules would automatically burst as a consequence of the movement of the arms, thus prolonging for a considerable time the effect of release of aromatic, balsamic or deodorant substances. Or else, the plasters may consist of the well-known nasal plasters, i.e., applicable on the nose and capable of keeping the nostrils dilated to favour breathing. In this case, the bursting of the micro-capsules may be caused voluntarily by the person who wears the said plaster, for example in order to obtain the release of a balsamic essence.

The adhesive plaster according to the invention comprises a flexible resistant substrate, on one surface of which is applied an adhesive that is capable of causing the said substrate to adhere to the skin of a person, the free surface of the adhesive being protected by a film of siliconized paper or the like, and is characterized in that at least a part of the other surface of said substrate is coated with a number of micro-capsules that enclose a liquid essence or a mixture of liquid essences.

Preferably, the micro-capsules are anchored to the surface of the substrate by means of resins that are soluble in water (in particular acrylic and/or polyvinylic resins). An aromatic essence is mixed to these resins so as to bestow on the plaster the same scent that will be obtained when the micro-capsules burst. The micro-capsules have a diameter of between 80 and 800 micron (in particular, of between 100 and 140 micron). The quantity of the mixture of the micro-capsules and the resin that fixes them to the substrate is between 10 g and 300 g (in particular, between 80 g and 150 g) per square meter of surface of substrate.

The adhesive plaster according to the invention is obtained with a method characterized in that micro-capsules are prepared which enclose liquid essences. Then a mixture is prepared made up of from 10 wt % to 80 wt % of said micro-capsules, from 0 wt % to 40 wt % of at least one liquid essence, and from 20 wt % to 90 wt % of a water-soluble resin, and characterized in that the said mixture is printed, by means of silk-screen printing, on at least part of a surface of a resistant and flexible substrate, on the other surface of which has previously been applied a layer of adhesive capable of causing the said substrate to adhere to the skin of a person.

Preferably the said mixture comprises 25 wt % of said micro-capsules, 33 wt % of said essence, 41 wt % of said resin, and 1 wt % of silica powder.

As essences that may be enclosed inside the micro-capsules, practically any essential oil may be used (either individually or mixed with other essential oils), such as eucalyptol, Scots pine, mugo pine, menthol, mint, orange blossom, lavender, citronella, paciulli, sage, ylang ylang, etc.

Mixtures having an excellent aromatic effect of a balsamic nature may, for example, be made up of two parts in weight of eucalyptol and one part in weight of Scots pine or mugo pine, or else of two parts of menthol and one part of mint.

It may be noted that, according to the known techniques of micro-encapsulation, the micro-capsules—after they have been obtained—are separated from the liquid solution in which they have been obtained, then they are washed with water, and silica powder is added to them to help them to dry out and to prevent the formation of lumps. The micro-capsules are then caused to pass through sieves which allow only the micro-capsules having the desired diameter to pass through, and finally they are dried out in an oven (for example, at 28° C. for eight hours) or at room temperature.

The dried micro-capsules thus obtained are then mixed with a liquid aromatic essence (or mixture of essences), with the water-soluble resin, and possibly with the silica powder, and the mixture thus obtained is applied on the surface of a sheet (made of fabric or made of a thin sheet of synthetic material) destined to form the resistant substrate from which the desired plaster will then be punched out, after a film of adhesive (capable of securing the substrate to the skin of the user of the plaster) coated with a protective sheet of siliconized paper or the like has been applied on the other surface.

If the substrate is made of a sheet of synthetic material (for example, made of plastic polyester or soft PVC), the silk-screen printing of the above-mentioned mixture is preferably preceded by a silk-screen printing operation of a gripping agent (for example, a normal water-soluble acrylic resin in quantities such as to leave on the strip between 10 g and 40 g of the said gripping agent per square meter of the surface of the sheet) having the function of favouring anchorage of the micro-capsules to the sheet itself.

Obviously, the frame used for silk-screen printing of the mixture containing the micro-capsules will have meshes of size greater than the size of the micro-capsules themselves. The quantity of mixture that will be deposited on the surface of the substrate will depend on the size of the said mesh; for example, if the micro-capsules have a diameter of 120 micron and the mesh of the printing frame has dimensions of 270 micron, it will be possible to spread 120 g of mixture on each square meter of the substrate. If the mesh itself has dimensions of 120 micron, on each square meter of the surface of the sheet it will be possible to spread approximately 10 g of mixture; if, instead, the mesh has dimensions of 500 micron, on each meter of the surface of the substrate up to 300 g of mixture containing the micro-capsules will be spread.

Figure 2:
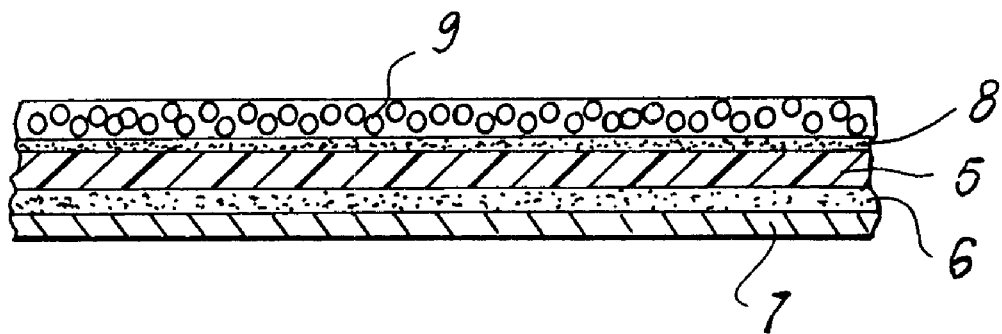

In order to make the characteristics of the invention easier to understand, a number of examples of embodiment of the invention will now be illustrated. These examples will have no limiting effect on the scope of the invention, and will be described with reference to the attached drawings, in which FIGS. 1 and 2 represent a cross section of two different plasters, shown in enlarged scale and out of proportion.

EXAMPLE 1

Assuming the aim is to prepare a plaster with deodorant aroma:

First of all an initial liquid mixture must be prepared consisting of the following essences: Sage 10 wt %—Orange blossom 20 wt %—Paciulli 20 wt %—ylang ylang 20 wt %—Lavender 30 wt %. This liquid mixture is then micro-encapsulated inside small spheres having a diameter of 150 micron, which are subsequently washed and to which silica powder is added (10 g per kg of micro-capsules); the micro-capsules are then filtered and dried at room temperature for 12 hours, all these operations being according to the micro-encapsulation procedures known to prior art.

Then a second mixture is prepared containing 20 wt % of the above micro-capsules, 10 wt % of the pure essences mixed together as for the first liquid mixture, 69 wt % of water-soluble acrylic resin, and 1 wt % of silica powder.

As substrate of the plaster, polyester fabric 1 (FIG. 1) is used, which is sufficiently soft and has a fine weft, and on one surface of which has been previously applied an adhesive layer 2 (for example, consisting of an acrylic adhesive) capable of causing the plaster to adhere to the skin, protected by a sheet 3 of siliconized paper. The substrate thus prepared may have the shape of a sheet having, for example, dimensions of 70×100 cm.

These sheets are printed, on the surface opposite the one on which the adhesive 2 has been applied, by means of the silk-screen technique, using the second mixture described above and employing a frame with a mesh of 300 micron. By means of this system, for each square meter of the sheet, 100 g of the second mixture are spread to form a layer 4, which comes out of the machine for silk-screen printing already dry.

The sheets thus obtained are then dinked to obtain plasters of the desired dimensions, for example 6×3 cm, which can then be applied under the armpits of persons. It has been found that the involuntary movement of the arms causes an automatic rubbing of the free surface of the plaster; this tends to cause progressive bursting of the micro-capsules, thus allowing the odoriferous essences to be released gradually. It has been found that the plaster described above maintains its deodorant function in an optimal manner for approximately 8 hours.

It has likewise been found that, probably on account of the structure of the fine-meshed fabric used according to the example illustrated above, the mixture with the micro-capsules is anchored in an optimal way to the fine-weft fabric 1 without presenting phenomena of detachment therefrom.

EXAMPLE 2

In a way similar to the one already described above, first of all an initial liquid mixture is prepared consisting of 65 wt % of eucalyptol and 35 wt % of Scots pine (or alternatively mugo pine). The said mixture is micro-encapsulated in spheres having a diameter of 120 micron, which are then washed and to which is added silica powder (10 g of silica per kg of micro-capsules). The micro-capsules are then dried in an oven at 28° C. for 8 hours.

A second mixture is then prepared made up of 25 wt % of the above-mentioned micro-capsules, 33 wt % of pure essences mixed as indicated for the first mixture, 41 wt % of a binding agent consisting of a water-soluble polyvinyl resin, and 1 wt % of silica powder.

Separately, a sheet having a format of 70×100 cm is prepared from a sheet 5 (FIG. 2) of transparent plastic polyester (or soft PVC), on which has been applied a layer 6 of adhesive (for example, acrylic resin suitable for adhering to skin) protected by a sheet 7 of siliconized paper. On the free surface of the sheet 5 there has first been applied—by means of silk-screen printing—a layer 8 of water-soluble acrylic resin (in the quantity of 30 g per square meter of surface) which has been made to dry in an oven at 30° C. for 10 minutes. This resin has the function of a gripping agent, in so far as the plastic polyester (just like PVC, PET and polyurethane) does not retain the mixture with the micro-capsules, which would thus tend to become detached from the sheet of polyester if the layer of gripping agent 8 were not provided.

Subsequently, on the layer 8 is applied, by means of silk-screen printing, a layer 9 of the second mixture described above, using a frame with a mesh of 270 micron which enables the depositing of 120 g of the said mixture over each square meter of the substrate. The sheets which have thus undergone silk-screen printing come out of the silk-screen printing machine, which is provided with an air-flow oven at approximately 30° C., already dry.

The sheets thus obtained are dinked to form plasters of approximately 6×2 cm, which may be applied over the nose or under the nostrils. In this case, the micro-capsules present in the layer 9 are burst as a result of voluntary rubbing of the external surface of the plaster, thus causing the odoriferous or balsamic substances enclosed therein to be released.

The nasal plasters may have any known profile or shape, and on them there may also be applied a bar of rigid PVC or equivalent material, as described in the patent application PCT/EP96/05818.

What is claimed is:

1. Adhesive plaster with microcapsules enclosing essences, comprising a flexible and resistant substrate, on one surface of which is applied an adhesive capable of causing the said substrate to adhere to the skin of a person, the free surface of the adhesive being protected by a protective sheet, wherein at least one part of the other surface of the said substrate is coated with a number of microcapsules containing a liquid essence or a mixture of liquid essences, and wherein said microcapsules have a diameter of between 100 and 140 micron.

2. Adhesive plaster according to claim 1, wherein said micro-capsules are anchored to the surface of the said substrate by a water-soluble resin.

3. Adhesive plaster according to claim 2, wherein said resin is selected from the group consisting of acrylic resins and polyvinyl resins.

4. Adhesive plaster according to claim 2, wherein said water-soluble resin is mixed with at least one aromatic essence.

5. Adhesive plaster according to claim 1, wherein said essence is selected from the group consisting of aromatic essences, balsamic essences, and deodorant essences.

6. Adhesive plaster according to claim 1, wherein the protective sheet comprises siliconized paper.

7. Adhesive plaster according to claim 1, wherein said microcapsules have a diameter of between 120 and 140 micron.

8. A method comprising adhering the adhesive plaster according to claim 1 underneath the armpits.

9. A method comprising adhering the adhesive plaster according to claim 1 to the nose at a location capable of keeping the nostrils dilated.

10. Method for the preparation of adhesive plasters with microcapsules enclosing essences, according to claim 1 characterized in that microcapsules are prepared that contain liquid essences, then a mixture is prepared containing from 10 wt % to 80 wt % of the said microcapsules, from 0 wt % to 40 wt % of at least one liquid essence, and from 20 wt % to 90 wt % of a water-soluble resin, and that using the silk-screen printing technique the said mixture is printed on at least one part of one surface of a resistant and flexible substrate, on the other surface of which has been previously applied a layer of adhesive capable of causing the said substrate to adhere to the skin of a person.

11. Method according to claim 10, characterized in that the said mixture contains from 0 wt % to 2 wt % of silica powder.

12. Method according to claim 11, characterized in that the said mixture contains 25 wt % of said microcapsules, 33 wt % of said essence, 41 wt % of said resin, and 1 wt % of silica powder.

* * * * *

UNITED STATES PATENT AND TRADEMARK OFFICE
CERTIFICATE OF CORRECTION

PATENT NO. : 6,399,192 B1
DATED : June 4, 2002
INVENTOR(S) : Pinna et al.

It is certified that error appears in the above-identified patent and that said Letters Patent is hereby corrected as shown below:

<u>Title page,</u>
Item [22], the PCT Filing Date is incorrect. Item [22] should read:
-- [22] PCT Filed: Jan. 26, 1998 --

Signed and Sealed this

Twenty-second Day of October, 2002

*Attest:*

JAMES E. ROGAN
*Attesting Officer*     *Director of the United States Patent and Trademark Office*